US00PP09741P

United States Patent [19]

Dümmen

[11] Patent Number: Plant 9,741

[45] Date of Patent: Dec. 10, 1996

[54] NEW GUINEA IMPATIENS PLANT NAMED 'HWD MELODIE'

[75] Inventor: Günter Dümmen, Rheinberg-Eversael, Germany

[73] Assignee: Dümmen Jungpflanzenkulturen, Rheinberg-Eversael, Germany

[21] Appl. No.: 516,182

[22] Filed: Aug. 17, 1995

[51] Int. Cl.[6] ..... A01H 5/00

[52] U.S. Cl. ..... Plt./87.6

[58] Field of Search ..... Plt./87.6

*Primary Examiner*—James R. Feyrer

*Attorney, Agent, or Firm*—Proprietary Rights International

[57] ABSTRACT

A new and distinct cultivar of New Guinea Impatiens plant named HWD Melodie, characterized by its medium light pink flowers; floriferousness; flowers that are resistant to rain damage; compact growth habit; freely branching plant habit; and dark green and glossy non-variegated foliage.

1 Drawing Sheet

The present invention relates to a new and distinct cultivar of New Guinea Impatiens plant, botanically known as *Impatiens hawkeri,* known as the variety Duemel, and hereinafter referred to by the cultivar name HWD Melodie.

The new cultivar is a product of a planned breeding program conducted by the inventor in Rheinberg, Germany. The objective of the breeding program was to develop a new light pink-flowered variety that was freely branching and with flowers resistant to rain damage.

The new cultivar originated from a cross made by the inventor of the cultivar Delias (U.S. Plant Pat. No. 7,838) as the male or pollen parent with the cultivar Tahiti (U.S. Plant Pat. No. 8,601) as the female or seed parent.

The cultivar HWD Melodie was discovered and selected by the inventor as a flowering plant within the progeny of the stated cross in a controlled environment in Rheinberg, Germany. Asexual reproduction of the new cultivar by terminal cuttings taken at Rheinberg, Germany, has shown that the unique featured of this new Impatiens are stabilized and reproduced true to type in successive generations of asexual reproduction.

The following traits have been repeatedly observed and are determined to be the unique characteristics of HWD Melodie. These characteristics in combination distinguish HWD Melodie as a new and distinct cultivar:

1. Medium light pink flowers.
2. Floriferous.
3. Flowers that are resistant to rain damage.
4. Compact growth habit.
5. Freely branching plant habit.
6. Dark green and glossy non-variegated foliage.

In comparison to the parent cultivar Delias, the new Impatiens has a more compact growth habit; flowers that are larger in diameter and more resistant to rain damage; and a lighter pink flower color. The flower color is similar to the parent cultivar Tahiti, however, the new Impatiens has flat, not cupped flowers, that are more resistant to rain damage, and the new Impatiens is more floriferous in comparison to cultivar Tahiti.

The accompanying colored photograph illustrates the overall appearance of the new cultivar, showing the colors as true as it is reasonably possible to obtain in colored reproductions of this type. The photograph comprises a top perspective view of a typical potted plant of HWD Melodie with one plant in a 15-cm container.

The cultivar HWD Melodie has not been observed under all possible environmental conditions. The phenotype may vary somewhat with variations in environment such as temperature and light intensity, without, however, any variance in genotype. The following observations, measurements and comparisons describe plants grown in Rheinberg, Germany, under commercial practice in a glass-covered greenhouse with day temperatures of 28° C. and night temperatures of 20° to 22° C. and light levels of 30,000 to 40,000 lux.

In the following description, color references are made to the Royal Horticultural Society Colour Chart except where general terms of ordinary dictionary significance are used.

Classification:

*Botanical.*—*Impatiens hawkeri.*

*Commercial.*—New Guinea Impatiens.

*Cultivar.*—HWD Melodie'.

Parentage:

*Male parent.*—'Delias' U.S. (Plant Pat. No. 7,838).

*Female parent.*—'Tahiti' (U.S. Plant Pat. No. 8,601).

Propagation:

*Type cutting.*—Terminal cuttings.

*Time to initiate roots.*—Summer: 27° C., 21 days; winter: 20° C., 28 days.

Plant description:

*General appearance.*—Rounded; dense; freely branching and compact growth habit; upright and spreading; moderate growth rate; suitable for 10 to 16-cm pots.

*Plant height.*—19 cm from soil level to top of plant plane.

*Foliage description.*—Shape: Elliptic with acuminate tip and attenuate base. Size: Length: 6.5 to 9 cm. Width: 2 to 3 cm. Texture: Smooth, glossy, and glabrous. Margin: Finely serrated, ciliate. Petiole length: 0.5 to 1.5 cm. Color: Young foliage, upper surface: 139A. Young foliage, under surface: Greener than 147B. Mature foliage, upper surface: 139A. Mature foliage, under surface: Greener than 147B. Veins, upper surface: 59B. Veins, under surface: 59B. Petiole: 59B.

*Stem description.*—Internode length: 3 cm. Stem color: 183B.

Flowering description:

*Flowering habit.*—Freely flowering.

*Natural flowering season.*—Year-round. Under summer conditions, plants flower 6 to 7 weeks after planting; under winter conditions, plants flower 9 to 11 weeks after planting.

*Flowers borne.*—Flower buds develop in apical leaf axils. Open flowers are displayed above the foliage.

*Quantity of inflorescences.*—Very floriferous; usually 10 to 12 buds and flowers per axil; usually more than 30 open flowers per plant open at one time.

*Flower longevity on plant.*—From opening, flowers will last 7 to 10 days.

*Flower diameter.*—5.5 cm.

*Flower depth (height).*—2 cm.

*Petals.*—Shape: Cordate. Quantity, arrangement: 5 petals overlapping. Aspect: Flat. Size: Length: 2.75 cm. Width: 3 cm. Texture: Smooth, satiny, and glabrous. Margin: Entire. Color: When opening: 62 C with eye, 66B. Upper surface: 62C with eye, 66B. Under surface: Predominantly 68A; base, 66B; towards margin, 69A; margin, almost white, 155D; streaks of 68A Fading to: Petal color does not fade.

*Peduncle.*—Angle: Erect. Length: 4.5 cm. Color: 185A.

*Flower bud.*—Shape: Ovoid with spur. Length: 1.5 cm. Diameter: 1 cm. Color: 67C.

*Spur.*—Shape: Needle-shaped, curved at end. Color: 59B.

*Sepals.*—Arrangement: Opposite. Quantity: 2. Shape: Ensiform with acuminate tip. Texture: Smooth and glabrous. Margin: Entire. Color: 184A.

*Reproductive organs.*—Androecium: Stamen number: 5. Anther color: Base, 67A; top, 11D. Pollen color: 11D. Gynoecium: Stigma color: 144D. Ovary color: 137A. Ovary size: 1 to 3 mm.

Disease resistance: No fungal, bacterial nor viral problems observed.

Seed development: Seed production is very rarely observed.

It is claimed:

1. A new and distinct cultivar of New Guinea Impatiens plant named HWD Melodie, as illustrated and described.

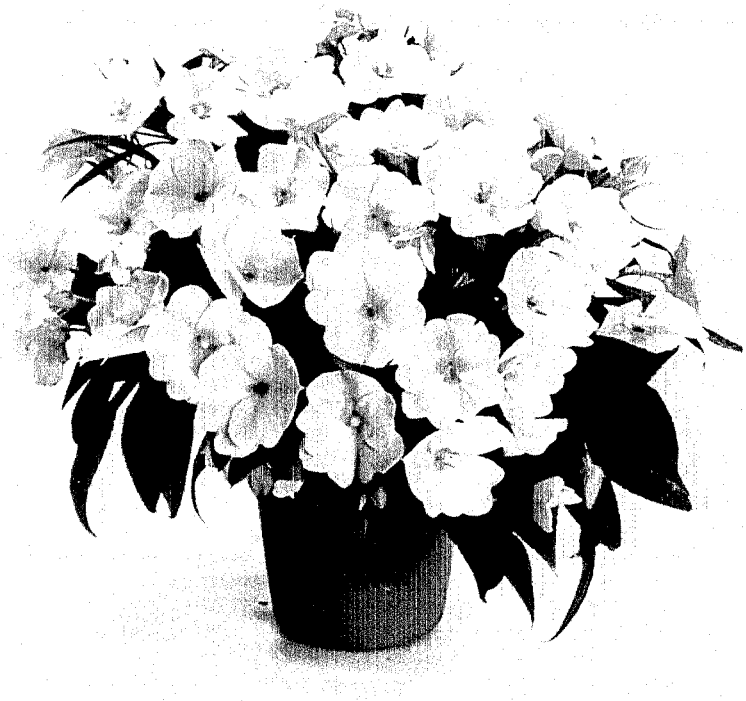

* * * * *